United States Patent [19]
Wilowski

[11] Patent Number: 4,792,798
[45] Date of Patent: Dec. 20, 1988

[54] REMOTE CONTROL SYSTEM FOR PULL-CORDS

[76] Inventor: Robert F. Wilowski, 74 Hickory Hill Rd., Simsbury, Conn. 06070

[21] Appl. No.: 33,214

[22] Filed: Apr. 2, 1987

[51] Int. Cl.$^4$ .................. H04Q 9/14; H01H 47/18
[52] U.S. Cl. .................. 340/696; 340/573; 340/636; 340/825.19; 361/182
[58] Field of Search .............. 340/573, 574, 539, 696, 340/548, 540, 825.19, 825.45, 825.69, 825.72, 636, 586; 361/182

[56] References Cited

U.S. PATENT DOCUMENTS

| | | | |
|---|---|---|---|
| 2,766,358 | 10/1956 | Davidson | 361/182 X |
| 3,686,672 | 8/1972 | Ishizuka | 361/182 |
| 3,827,039 | 7/1974 | Agnese | 340/586 |
| 3,910,432 | 10/1975 | Browne et al. | 414/539 |
| 3,971,028 | 7/1976 | Funk | 340/825.69 X |
| 4,044,323 | 8/1977 | Sleger | 335/240 |
| 4,056,815 | 11/1977 | Anderson | 340/539 |
| 4,057,794 | 11/1977 | Grossfield | 340/825.45 X |
| 4,121,160 | 10/1978 | Cataldo | 340/539 X |
| 4,242,668 | 12/1980 | Herzog | 340/539 |
| 4,276,939 | 7/1981 | Atack | 169/60 |
| 4,307,768 | 12/1981 | Anderson | 160/84.1 |
| 4,365,237 | 12/1982 | Knight | 340/586 X |
| 4,622,544 | 11/1986 | Bially et al. | 340/573 X |
| 4,706,726 | 11/1987 | Nortoft | 160/168 R |

*Primary Examiner*—Glen R. Swann, III
*Assistant Examiner*—Thomas J. Mullen, Jr.

[57] ABSTRACT

A remote control for pull-cord stations in hospitals, convalescent homes, and multi-unit housing for the elderly consists of a portable transmitter and an activator unit. The small, battery-powered radio transmitter is worn on a necklace. The compact activator unit is hung on the wall and plugged into an electrical outlet. The pull-cord is tied with a simple knot to the activator unit. A person requiring emergency assistance who is unable to get to the pull-cord summons help by pressing the button on the transmitter. A loud buzzer in the activator unit announces that the distress signal has been received and the cord has been pulled and that help is on the way.

8 Claims, 2 Drawing Sheets

REMOTE CONTROL SYSTEM FOR PULL-CORDS

CROSS REFERENCE TO RELATED APPLICATIONS

Patent Disclosure No. 160067, Remote Control for Pull-Cords submitted to the Comissioner of Patents and Trademarks on Dec. 3, 1986.

BACKGROUND OF THE INVENTION

It is required that patients in hospitals and convalescent homes and residents of multi-unit housing for the elderly have a call system with which to call for assistance or emergency help from nurses or attendants. Many such call systems utilize a pull-cord station. A pull-cord station consists of a wall-mounted switch with a cord connected to it which hangs to the floor. Pulling the cord activates the switch and its associated alarm circuitry.

Persons are only protected by such a pull-cord station if they are within reach of a pull-cord or are able to get to one. Accidents can occur anywhere and are often immobilizing. Therefore, it may be difficult or impossible for a person to reach a pull-cord quickly or at all in an emergency if, for example, he or she is in another room and/or is unable to move.

The remote control for pull-cords to be described here is intended to enable a person to activate a pull-cord station by wireless remote control from anywhere in the living area. No pull-cord stations up until now have had a remote control capability. Therefore, providing essential, wide area protection in care facilities with pull-cord stations has required extensive reconstruction of the alarm circuit.

U.S. Pat. No. 4,605,927 discloses a controller responsive to an FM transmitter which must be hard-wired into a call-system. U.S. Pat. No. 3,971,028 discloses a radio responsive rachet relay which would require hard-wiring if applied to a call system. U.S. Pat. No. 4,418,334 discloses a call system with no remote control capability. U.S. Pat. No. 3,827,039 discloses a portable alarm utilizing a pull-cord but which is too large to constantly carry and which is lacking in signal transmitting features required of a hospital call system. U.S. Pat. No. 4,355,309 discloses a digitally encoded transmitter which controls a relay circuit that would require hard-wiring if applied to a call system. U.S. Pat. No. 4,298,863 discloses a call system that has no remote control and which activates electrical contacts that must be hard-wired to an existing call system.

Other easily portable distress signalling devices are available which emit a loud alarm signal. These devices do not communicate directly with the proper personnel and cause a major local disturbance. Other aid summoning systems consist of remote controlled dialing machines that deliver a digital message over telephone lines. Such systems must be hard-wired to an existing call system. These systems also depend upon unreliable telephone lines and require expensive digital message receiving equipment and staff training.

No device has been available until now to easily and inexpensively convert a pull-cord station to a remotely controllable, broad protection, call system.

SUMMARY OF THE INVENTION

In this invention, the cord of the pull-cord station is connected to a pull-type solenoid that can be activated by a small, easily portable, battery-powered radio transmitter. A person wears the transmitter on a necklace at all times whenever he or she is in the living area. When the person pushes the button on the transmitter, a signal is sent to a radio receiver which activates the solenoid which in turn pulls the cord signalling for help. A buzzer also sounds when the solenoid is activated so that the person transmitting the distress signal will know that the cord has been pulled and help is on the way. The pull-cord station remains activated until it is manually reset by the responding nurse or attendant. The system employs digitally encoded transmission signals so that each person's transmitter will activate only that person's receiver and pull-cord station. The condition of the transmitter's battery is constantly monitored automatically so that it will be replaced when necessary. A small power indicator lamp assures that the receiver and solenoid are ready.

The great advantage of this invention over related prior art is that this system employs a pull-cord station activator unit that is not hard-wired into the existing alarm circuit. The activator unit rather is completely self-contained in a box that simply plugs into an electrical outlet, is simply tied to the pull-cord with a knot, and which box may be easily mounted and removed from a wall location below the pull-cord station.

These unique installation qualities greatly reduce the time, skill, and therefor the expense required for installation. The disruption of the user's living area is also reduced since building alterations need not be made to install wiring. The care facility staff need not adjust to a new alarm annunciating system since the existing system has been retained. Easy mounting and removal of the activator unit enables care facilities to provide the extra protection afforded by this system to those high risk persons requiring it. The activator unit can be easily removed when it is no longer required at a particular pull-cord station. Thus, costs are further reduced because each activator unit can be rotated throughout the care facility as needed.

Another advantage of this invention is that the pull-cord can still be pulled by hand as it was before being connected to the remote control activator unit. This is important because call stations are required by law in care facilities and therefore must be retained.

DESCRIPTION OF THE PREFERRED EMBODIMENT

Figure 1:
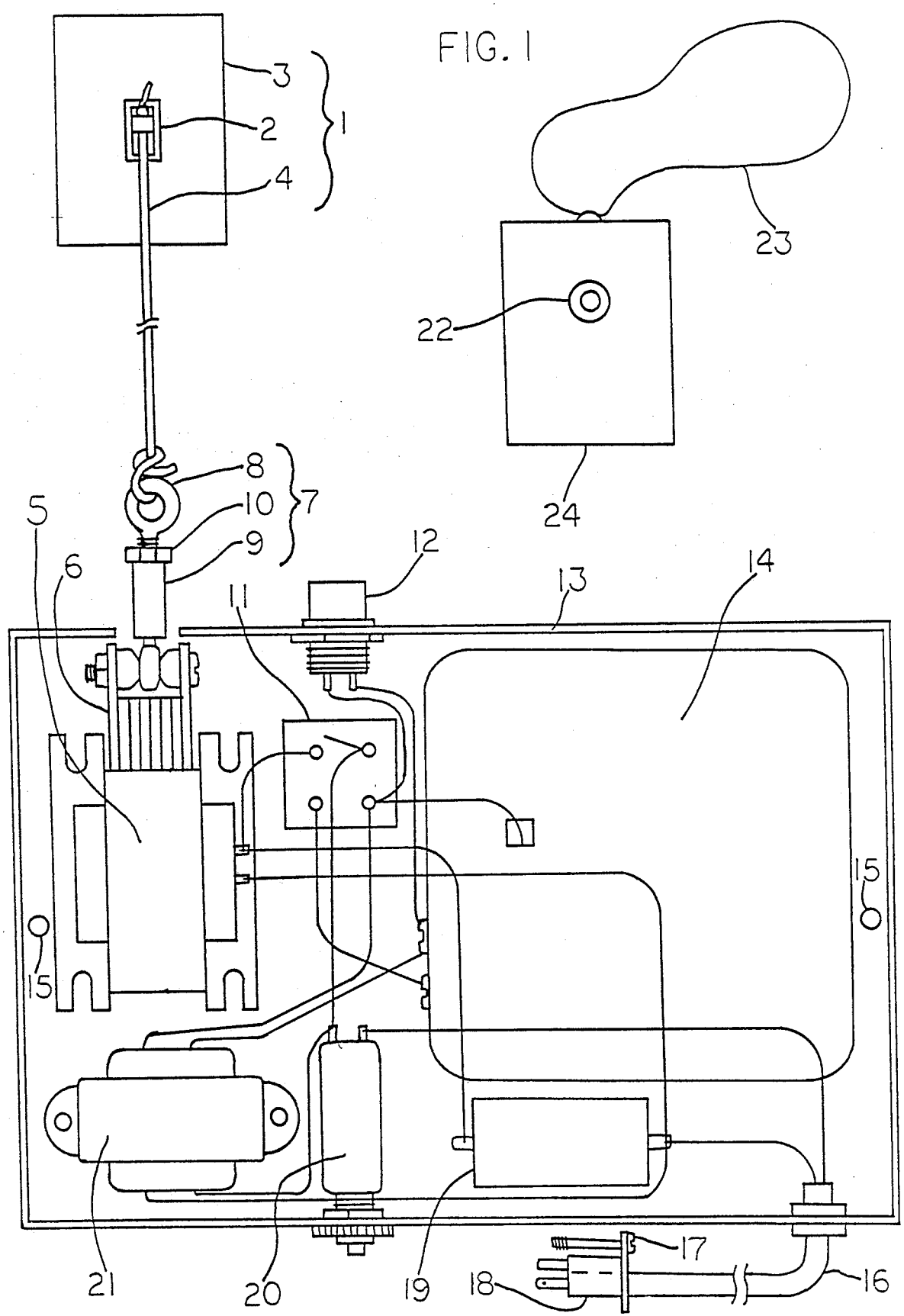
FIG. 1 is a front view of the invention with the cover removed showing it connected to a pull-cord station.

Referring to FIG. 1, the pull-cord station 1 consists of a switch 2 mounted to the wall by a mounting plate 3 with one end of a cord 4 connected to said switch. To add remote control capability to the pull-cord station 1, the other end of the cord 4 is tied with a knot to the eyebolt 8 of the adjustable linkage 7 which is connected to the plunger 6 of the solenoid 5. The adjustable linkage 7 consists of the eyebolt 8, an internally threaded spacer 9 and a lock nut 10. The spacer 9 is connected to the plunger 6 of the solenoid 5. Screwing the eyebolt 8 into the spacer 9 raises the plunger 6 and increases its stroke. Screwing the eyebolt 8 out of the spacer 9 lowers the plunger 6 and decreases its stroke. The lock nut 10 serves to prevent the eyebolt 8 from turning once the proper stroke length has been attained. The stroke of the plunger 6 must match the stroke of the pull-cord switch 2. Such easy attachment and adjustment makes this invention compatible with all types of pull-cord stations. The solenoid 5 is also sufficiently strong and has the stroke capacity to activate all types of pull-cord stations.

A buzzer 19 is connected in parallel with the solenoid 5 so that whenever the solenoid 5 is activated said buzzer is also activated. Both the solenoid 5 and the buzzer 19 are actuated by a self-contained normally-open relay 11. When the self-contained relay 11 is closed, the solenoid plunger 6 pulls the cord 4 activating the pull-cord switch 2 and the buzzer 19 sounds.

Figure 2:
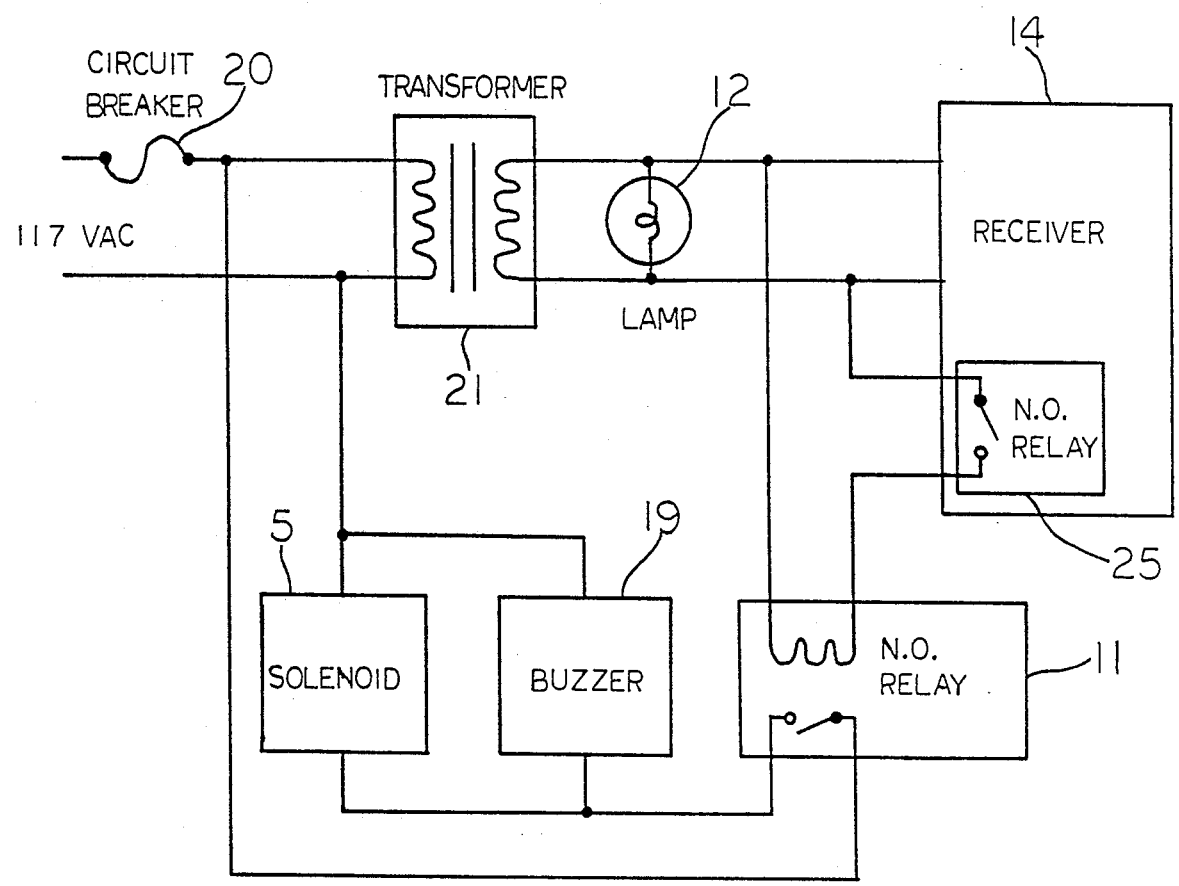
FIG. 2 is a schematic block diagram of the invention.

Referring to FIG. 2, the self-contained relay 11 is itself activated by the normally-open receiver relay 25 contained and controlled by the radio receiver 14. A radio transmitter 24 communicates with the receiver 14 to activate the receiver relay 25. The transmitter 24 has a push-button switch 22 which, when depressed, causes a radio signal to be transmitted.

Thus, referring to FIG. 1 and FIG. 2 together, when the push-button 22 on the transmitter is depressed, the receiver 14 activates its relay 25 which in turn activates the self-contained relay 11 which then energizes both the solenoid 5 and the buzzer 19. The cord 4 is pulled, the pull-cord station 1 is activated, and help is summoned.

Referring to FIG. 1, the electrical power is obtained by connecting the electrical cord 16 to a standard 117 VAC electrical outlet via a plug 18. The plug 18 is prevented from being accidentally disconnected from the electrical outlet by a plug restraint 17. A step-down transformer 21 is used to power the receiver 14, the self-contained relay 11, and the power indicator lamp 12. Circuit overload protection is provided by a circuit breaker 20 which has a push-button reset. The box 13 which encloses the pull-cord station activator unit is mounted to the wall using two mounting holes 15. The transmitter 24 has an attached chain 23 to be worn around the user's neck.

Examples of common manufactured components which have been found to be most suitable for use in this invention are as follows: The pull-cord switch 2 is an on-off switch such as that described in U.S. Pat. No. 2,743,330. The solenoid 5 operates at 117 VAC and has a pull force of 6.35 pounds and a ¾ inch maximum stroke. The buzzer 19 operates at 117 VAC and emits an 85 dB tone measured at three feet. The self-contained relay 11 is a single-pole double throw relay with contacts rated at 5 amps and 120 VAC. The transformer 21 has a 117 VAC primary winding and an output of 14 VAC and 0.35 amps. The lamp 12 operates at 14 VAC, consumes 0.08 amps and has a 50,000 hour life. The box 13 is molded from impact resistant, KJW grade ABS plastic with outside dimensions of 8.0 in. by 6.25 in. by 2.5 in. The receiver 14 is a single channel digital receiver with a normally-open relay output and 256 unique code combinations. The receiver operates at 14 VAC and consumes 10 mA on standby and 40 mA when operating. The transmitter 24 is a single channel digital transmitter which operates on a 12 VDC battery and which notifies the user when its battery must be replaced. The transmitter also has 256 unique transmitting codes.

Although one detailed embodiment of the invention is illustrated in the drawings and previously described in detail, this invention contemplates any configuration, design and relationship of components which will function in a similar manner and which will provide the equivalent result.

I claim:

1. A remote control system for operating a pull cord associated with a wall-mounted pull cord station which has a two-position switch normally maintained in a first position and activating the pull cord station in a second position, comprising:
   (a) a solenoid having a plunger which moves when the solenoid is energized;
   (b) an adjustable linkage connected to said plunger and movable therewith;
   (c) a radio receiver for receiving transmitted radio frequency signals and energizing said solenoid in response thereto;
   (d) a portable, battery powered radio transmitter for transmitting radio frequency signals and being actuated by means of a push button; and
   (e) a portable, self-contained housing adapted to be mounted on a wall so as to be located proximate to the pull cord station, the housing having therein said solenoid and said receiver; wherein,
   said pull cord is attached at one end to said switch and at a second end to said linkage, so that when the transmitter is actuated a signal is transmitted to said receiver causing the solenoid to become energized whereby the plunger moves the linkage to pull said pull cord, whereby said switch is moved from said first position to said second position.

2. A remote control system as recited in claim 1, further comprising a buzzer housed with said solenoid and said receiver and energized when the solenoid is energized.

3. A remote control system as recited in claim 1, wherein said housing is equipped with a flexible power cord for connection to an AC power source.

4. A remote control system as recited in claim 1, wherein said linkage includes an eyebolt and said pull cord is tied in a knot to said eyebolt.

5. A remote control system as recited in claim 1, further comprising a relay responsive to the receiver receiving a transmitted signal to energize said solenoid and said buzzer.

6. A remote control system as recited in claim 1, wherein said transmitter transmits digitally coded signals, and said receiver is adapted to receive said digitally coded signals.

7. A remote control system as recited in claim 1, wherein said transmitter comprises means to indicate a low battery condition.

8. A remote control system as recited in claim 1, wherein said transmitter may be carried by an individual by means of a chain worn around said individual's neck and attached to said transmitter.

* * * * *